(12) United States Patent
Weil et al.

(10) Patent No.: US 6,360,125 B1
(45) Date of Patent: Mar. 19, 2002

(54) CPR PROTECTOR

(75) Inventors: Max Harry Weil, Northbrook, IL (US); Wanchun Tang, Palm Desert; Joe Bisera, Camarillo, both of CA (US)

(73) Assignee: Institute of Critical Care Medicine, Palm Springs, CA (US)

( * ) Notice: Subject to any disclaimer, the term of this patent is extended or adjusted under 35 U.S.C. 154(b) by 0 days.

(21) Appl. No.: 09/217,008

(22) Filed: Dec. 21, 1998

(51) Int. Cl.$^7$ .................................................. A61N 1/39
(52) U.S. Cl. .............................. 607/5; 607/152; 607/3; 607/63; 607/142; 600/393
(58) Field of Search .................... 607/142, 149, 607/152, 3, 2, 5, 63; 600/372, 382, 388, 389, 393

(56) References Cited

U.S. PATENT DOCUMENTS 4,664,118 A * 5/1987 Batters ........................ 607/46
5,466,244 A * 11/1995 Morgan ........................ 607/50
6,178,357 B1 * 1/2001 Gliner et al. ................ 607/142

* cited by examiner

*Primary Examiner*—Kennedy Schaetzle
(74) *Attorney, Agent, or Firm*—Leon D. Rosen

(57) ABSTRACT

Apparatus is provided for use during the treatment of a victim undergoing cardiac arrest, to facilitate treatment by chest compression as well as by shocks from an automatic defribrillator. The apparatus includes a sheet of dielectric material that covers much of the victim to electrically isolate a rescuer who is performing chest compressions, from the victim to whom electric shocks are being delivered. Defribrillator electrodes are mounted on the lower face of the sheet and are connected to the defribrillator. The sheet extends down along the sides of the victim to isolate the rescuer, who is either standing or kneeling beside the victim to apply chest compressions.

8 Claims, 2 Drawing Sheets

CPR PROTECTOR

BACKGROUND OF THE INVENTION

Automatic defribrillators use a pair of electrodes on the chest area of the victim, to receive EKG (electrocardiogram) signals from the victim, and to deliver high voltage pulses to the victim when the defribrillator circuit detects a condition indicating that a shock would be beneficial. It is known that precordial compressions, or compressions of the middle of the lower chest area, are beneficial to the victim in cardiac arrest. Because chest compressions can affect the EKG signals, previous procedures required a rescuer to not apply chest compressions during perhaps 25 seconds while the automatic defribrillator senses and evaluates EKG signals. Applicant has found EKG signals from the electrodes attached to the victim's chest, can be processed so signal components arising from chest compressions can be filtered out. This allows chest compressions to continue up to the time when electric shocks are applied, and allows chest compressions to continue as soon as the shocks are over.

It is common for the defribrillator to sound a warning immediately before the application of electric shocks, to warn rescuers to move away from the victim. However, if the rescuer is kneeling over the victim, then a longer warning time must be provided, or the danger of the rescuer being shocked increases. Apparatus that protects the rescuer from a high voltage shock applied to the victim, provides for the rescuer's safety and allows for uninterrupted chest compressions without fear of shocking the rescuer, thereby improving the success of cardiac resuscitation.

SUMMARY OF THE INVENTION

In accordance with one embodiment of the present invention, apparatus is provided for use by a rescuer who resuscitating a victim with cardiac arrest symptoms in conjunction with an automatic defribrillator, which protects the rescuer from electric shocks applied to the victim. The apparatus includes a sheet of flexible and electrically insulative material, which blocks the passage of current even when a voltage of hundreds of volts is applied between opposite faces of the sheet. A pair of electrodes lie below the lower face of the sheet to engage locations on the chest of the victim, while the upper face of the sheet isolates the rescuer from the victim's body. The sheet preferably extends to a side of the victim where the rescuer is, and down along the side of the victim, to prevent shocks being transmitted to the knee area of the rescuer who is applying chest compressions. A weight at the side of the sheet and preferably at opposite sides of the sheet, helps keep the side of the sheet in place. The sheet preferably has a part that extends over the head of the victim and that has a hole for at least the nose and mouth of the victim. A closeable slit provides ready access to the electrodes.

The novel features of the invention are set forth with particularity in the appended claims. The invention will be best understood from the following description when read in conjunction with the accompanying drawings.

DESCRIPTION OF THE PREFERRED EMBODIMENTS

Figure 1:
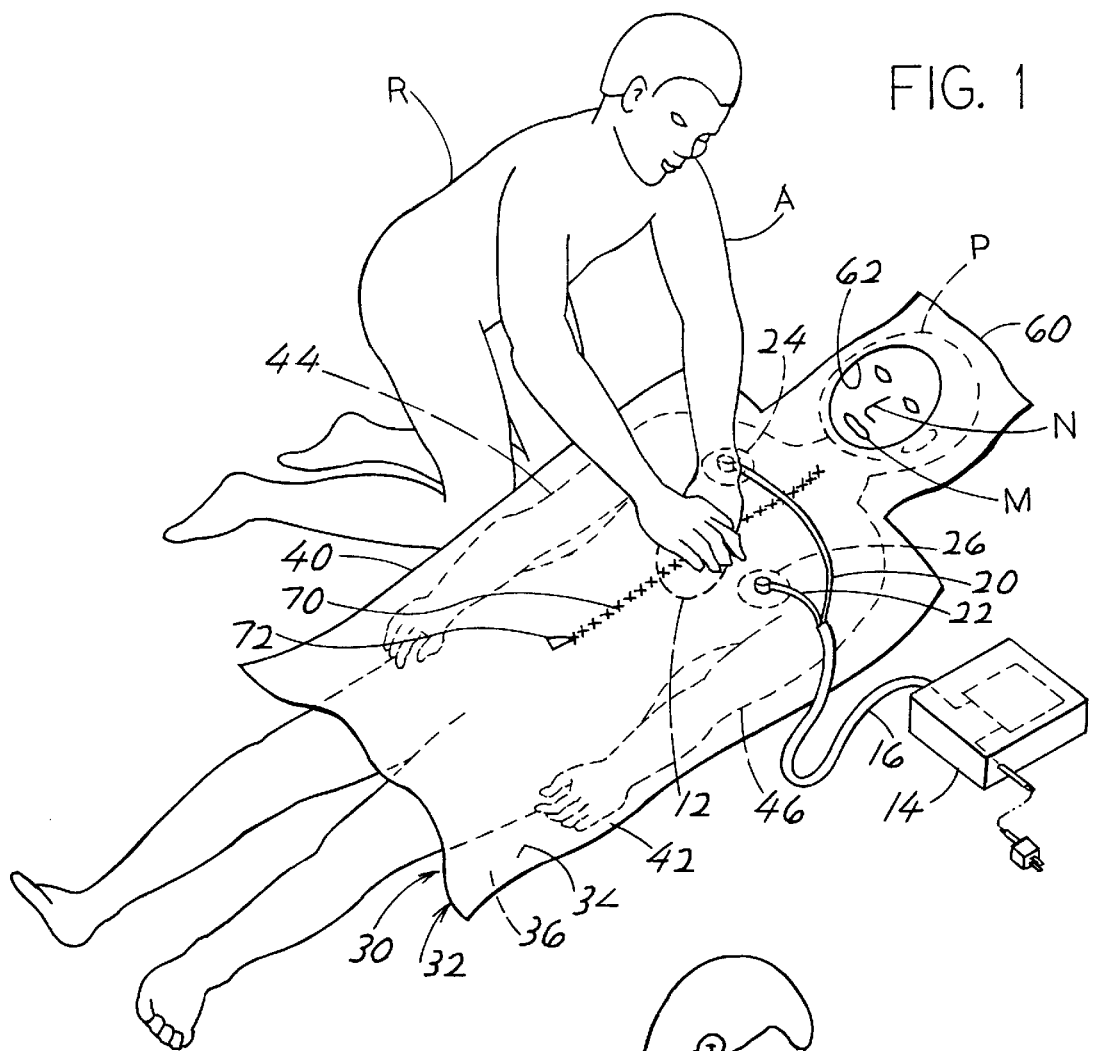
FIG. 1 is an isometric view of a victim and rescuer, with apparatus of the present invention covering the victim.
Figure 5:
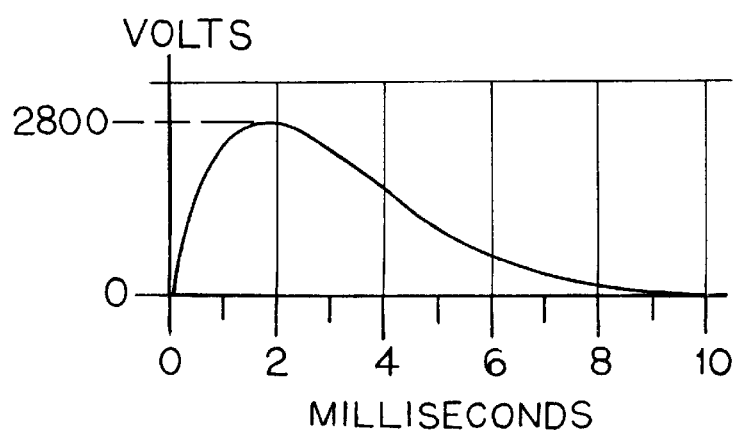
FIG. 5 is a graph showing variation in voltage with time of a typical defribrillation pulse applied by the defribrillator of FIG. 1 to the electrodes of FIG. 1.

FIG. 1 illustrates a patient or victim P who has symptoms of cardiac arrest, and who is being treated by a rescuer R, who is performing precordial compressions, that is, compressions at the lower chest area 12, in conjunction with an automatic defribrillator 14. The defribrillator has a cable 16 with wires 20, 22 having conductors therein, which are connected to first and second electrodes 24, 26. The electrodes are applied to the chest of the victim at predetermined locations. The rescuer applies downward forces or compressions to the area 12 of the victim, and also may blow air into the mouth M of the victim by mouth-to-mouth resuscitation or through a rubber bellows. The automatic defribrillator 14 receives EKG (electrocardiogram) signals from the electrodes 24, 26 to analyze the condition of the victim. When the circuitry in the defribrillator determines that an electric shock would be beneficial, the defribrillator sounds an alarm to warn the rescuer and other persons who may be affected. Then a high voltage electric pulse, such as of the type shown in FIG. 5, is applied through the electrodes to the victim.

Applicant has developed apparatus which enables the automatic defribrillator 14 to filter out signals resulting from chest compression by the rescuer, so that chest compression and/or the blowing of air into the victim's mouth may be continued for up to perhaps three seconds prior to a high voltage electric shock. It is preferable that the warning time be as small as feasible to enable continued chest compression as long as possible. However, the rescuer must be protected from high voltage shocks that he/she would receive if in physical contact with the victim's body caused by the high voltage applied through the electrodes to the victim's heart.

In accordance with the present invention, applicant provides an apparatus 30 that includes a sheet 32 of a flexible dielectric, or highly insulative, material to electrically shield the rescuer from the victim. The sheet prevents the passage of significant currents through it when a voltage of a plurality of hundreds of volts, and preferably at least a thousand volts, is applied between upper and lower faces 34, 36 of the sheet. The sheet covers the lower chest area 12 which is compressed by the rescuer. Thus, even if the rescuer is pressing against the victim (through the sheet) at the time when a high voltage pulse is applied between the electrodes 24, 26, the rescuer will not be shocked by currents transmitted to the rescuer's arms A. The electrodes 24, 26 are attached to the sheet 32 and lie under the lower face 36 of the sheet. This prevents the rescuer and adjacent equipment from contact with the electrodes and conductive material, which is hazardous when a high voltage pulse is applied to the electrodes.

Figure 2:
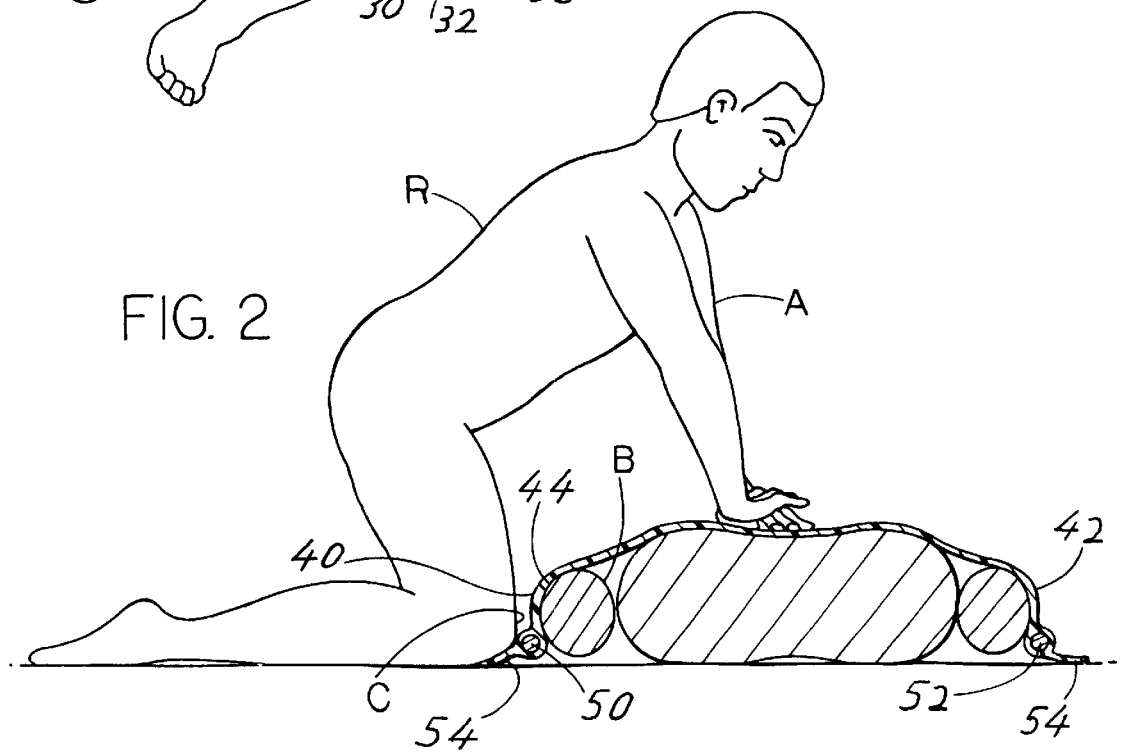
FIG. 2 is a sectional view of the victim, rescuer, and apparatus of the invention of FIG. 1.

The sheet has opposite side portions 40, 42 that lie beside the opposite sides 44, 46 of the victim in FIGS. 1 and 2, at his arms B. It can be seen from FIG. 2, that the knee area C of the rescuer may lie very close to a first side 44 of the victim. The first side 40 of the sheet covers the side of the victim and preferably extends onto the ground. Applicant provides a weight 50, 52 at each side portion 40, 42 of the sheet to assure that the side portion remains draped over the victim's side. The weights can be formed from bars of metal over which the insulative sheet has been wrapped. The weights may rest on the ground, and sheet portions 54 extend beyond the weights.

Most of the sheet covers the torso of the victim, down to perhaps the victim's knees. The sheet preferably has a head part 60 with an opening 62 that uncovers at least the mouth and nose of the victim. The head part give some protection against a rescuer or nearby equipment accidentally touching the head of the victim at a location around the opening.

Applicant provides a slit 70 with a closure 72 such as a plastic zipper or Velcro strips, to enable easy access to the electrodes 24, 26.

Figure 4:
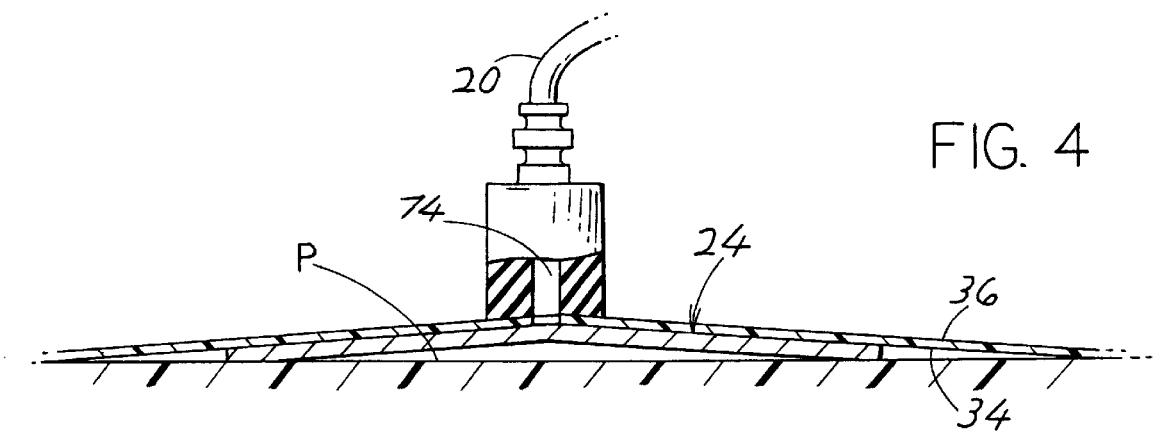
FIG. 4 is a sectional view of the apparatus of FIG. 1, showing an electrode and a portion of the insulative sheet.

FIG. 4 illustrates one electrode 24 which is pressing against the victim P and which is connected through a conductor 74 of a wire 20 to the defribrillator.

Figure 3:
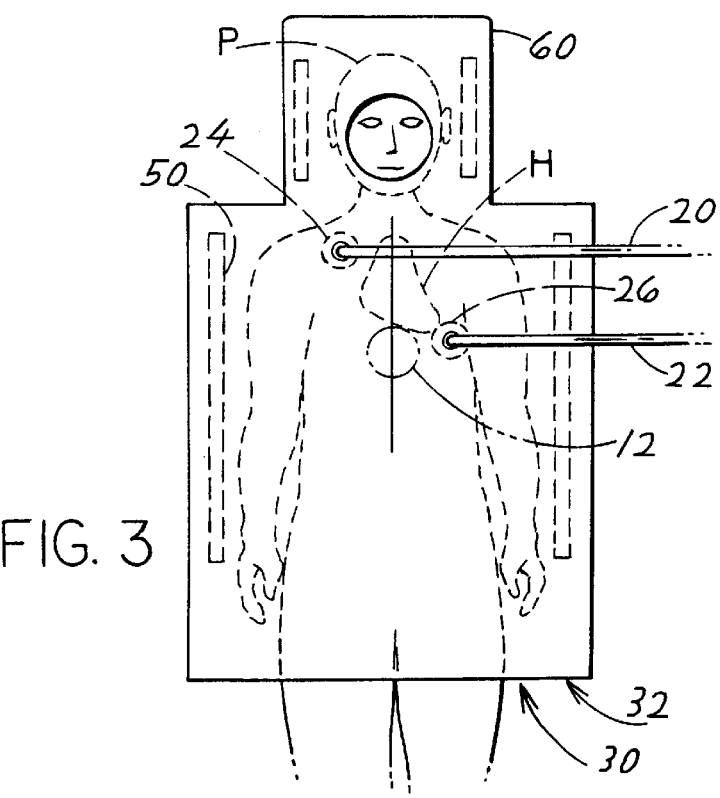
FIG. 3 is a plan view of the apparatus of the invention before its use with a victim, and also showing, in phantom lines, a victim over whom the apparatus is applied.

FIG. 3 shows the shape of the dielectric sheet 32 of the apparatus 30 relative to a victim P prior to application of the sheet to the victim. The electrodes 24, 26 are already placed to lie on opposite sides of the heart H of the victim, with the electrode 24 lying near the right shoulder of the victim and the second electrode 26 lying at the opposite side of the victim at about the middle of the lower chest area whose middle is indicated at 12. The sheet has a width of about 40 inches (30 to 55 inches) to readily extend across the width of most victims and preferably a few inches along the floor, without being cumbersome.

Thus, the invention provides apparatus for use by a rescuer who is treating a victim with cardiac arrest symptoms in conjunction with an automatic defribrillator. The apparatus includes a sheet of flexible and electrically insulative, or dielectric, material which has upper and lower faces and which prevents the passage of current therethrough when a voltage of a plurality of hundreds of volts and preferably at least one thousand volts, is applied. A pair of electrodes are attached to the sheet with each electrode having a conductive lower surface that is accessible from a lower face of the sheet but preferably not the upper face of the sheet. The sheet covers at least an area between and near the electrodes to cover at least the middle lower chest area 12 of the victim, where chest compressions are applied by the rescuer (either with his hands or with equipment). The sheet preferably extends to and covers at least one side of the victim and preferably both sides of the victim to protect the knee area or other area of the rescuers adjacent to the victim. The sheet can include a part that covers the head of the victim and that has an opening to expose at least the mouth and nose area of the victim. Weights can hold the sides of the sheet down around the victim. A closeable slit enables access to the electrodes without requiring removal of the sheet Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. Apparatus for use by a rescuer who is treating a victim with cardiac arrest symptoms by at least chest compressions, in conjunction with a defibrillator which has a circuit and a plurality of conductors for delivering an electric shock to the victim's heart, comprising;

a sheet of insulative material which can be placed between the victim's lower chest area and a hand of the rescuer and that prevents the passage of a shocking current between said chest and hand when a voltage of a plurality of hundreds of volts is established between them, said sheet having a lower surface for lying on the victim;

a pair of electrodes attached to said sheet and lying on said lower surface of said sheet to contact locations on the victim near the victim's heart;

said sheet including a side portion that extends beyond an adjacent one of said electrodes sufficiently that when said adjacent one of said electrodes lies on top of the victim, the side portion covers a side of the victim to guard the body of the rescuer that may be pressed toward the side of the victim.

2. The apparatus described in claim 1 including;

a weight attached to said sheet at said first side portion of said sheet, to keep the sheet hanging closely adjacent to the side of the victim.

3. Apparatus for use by a rescuer who is treating a victim with cardiac arrest symptoms by at least chest compressions applied to the middle of the lower chest area, in conjunction with electric shock currents, comprising:

a sheet of flexible and electrically insulative material which has upper and lower faces;

a pair of electrodes attached to said sheet with each electrode having a conductive lower surface that is accessible from a lower one of said faces of said sheet, and with each electrode capable of passing an electrical pulse from a defibrillator to a victim;

a defibrillator which generates voltage pulses of hundreds of volts to shock the heart of the victim, said defibrillator having a pair of conductors connectable to said electrodes;

said sheet having a side portion that extends beyond an adjacent one of said electrodes sufficiently that when said adjacent one of said electrodes lies on top of the chest of the victim the side portion covers a side of the victim to protect a rescuer who is positioned at said side of the victim.

4. The apparatus described in claim 3 wherein:

said sheet includes a torso part that covers most of the torso of the victim and a head part that covers the head of the victim, with said head part having an opening of a plurality of inches wide to leave open at least the mouth and nose of the victim.

5. The apparatus described in claim 3 wherein:

said sheet has a slit extending along a middle of the sheet to extend from near the neck to near the abdomen of the victim, to provide access to said electrodes.

6. The apparatus described in claim 3 wherein:

said sheet has a side part for covering the side of the victim, with said side part having a weight to hold down the side part so the rescuer's knee areas can press against the victim only through said side part.

7. The apparatus described in claim 3 wherein:

said sheet has a width of about 40 inches, to extend across the width of most victims without being cumbersome.

8. Apparatus for use by a rescuer who is treating a victim with cardiac arrest symptoms by at least chest compressions applied to the middle of the lower chest area, in conjunction with a defibrillator which has a plurality of conductors for carrying electric shock currents from the defibrillator to the victim's chest to shock the victim's heart, comprising:

a sheet of flexible and electrically insulative material which has upper and lower faces;

a pair of electrodes attached to said sheet with each electrode having a conductive lower surface that is accessible from a lower one of said faces of said sheet;

said sheet having a width of about 40 inches to extend across the width of most victims without being cumbersome and to cover at least the middle of the lower chest and a first side of the victim to protect a rescuer who is positioned at said first side.

* * * * *